(12) United States Patent
Roehn

(10) Patent No.: US 8,979,493 B2
(45) Date of Patent: Mar. 17, 2015

(54) FLUID PUMP

(75) Inventor: Daniel Roehn, Berlin (DE)

(73) Assignee: ECP Entwicklungsgesellscaft mbH, Berlin (DE)

(*) Notice: Subject to any disclaimer, the term of this patent is extended or adjusted under 35 U.S.C. 154(b) by 799 days.

(21) Appl. No.: 13/255,664

(22) PCT Filed: Mar. 18, 2010

(86) PCT No.: PCT/EP2010/001889
§ 371 (c)(1),
(2), (4) Date: Nov. 2, 2011

(87) PCT Pub. No.: WO2010/105854
PCT Pub. Date: Sep. 23, 2010

(65) Prior Publication Data
US 2012/0039711 A1 Feb. 16, 2012

Related U.S. Application Data

(60) Provisional application No. 61/161,125, filed on Mar. 18, 2009.

(30) Foreign Application Priority Data

Mar. 18, 2009 (EP) .................................. 09075127

(51) Int. Cl.
*A61M 1/12* (2006.01)
*F04D 3/00* (2006.01)
(Continued)

(52) U.S. Cl.
CPC ............. *A61M 1/101* (2013.01); *F04D 3/00* (2013.01); *F04D 29/181* (2013.01); *F04D 29/247* (2013.01); *A61M 1/1024* (2014.01); *A61M 1/125* (2014.02)
USPC .......................... 416/88; 416/132 A; 416/143

(58) Field of Classification Search
CPC ........... F04D 7/00; F04D 3/00; F04D 29/247; F04D 29/18; F04D 29/181; F04D 29/305; F04D 29/382
USPC .......... 416/87–89, 131, 132 R, 132 A, 134 R, 416/135–136, 140, 142–143, 230, 240
See application file for complete search history.

(56) References Cited

U.S. PATENT DOCUMENTS

| | | | |
|---|---|---|---|
| 3,033,293 A * | 5/1962 | Bihlmire | 416/240 |
| 3,510,229 A | 5/1970 | Smith et al. | |
| 3,568,659 A | 3/1971 | Karnegis | |
| 3,802,551 A | 4/1974 | Somers | |
| 3,812,812 A | 5/1974 | Hurwitz | |

(Continued)

FOREIGN PATENT DOCUMENTS

| CA | 1008330 A1 | 4/1977 |
|---|---|---|
| CA | 2311977 A1 | 12/2000 |

(Continued)

OTHER PUBLICATIONS

International Search Report and Written Opinion, from PCT/EP10/001889, mailed May 12, 2010.

(Continued)

*Primary Examiner* — Edward Look
*Assistant Examiner* — Jesse Prager
(74) *Attorney, Agent, or Firm* — Marshall & Melhorn, LLC

(57) ABSTRACT

The invention relates to a fluid pump, in particular liquid pump, with a rotor, with a rotor shaft (11) and with at least one rotor blade for delivering the fluid, wherein the rotor with regard to its diameter may be changed between a first, compressed condition, and a second expanded condition, wherein the at least one rotor blade comprises at least two erection elements (12, 13, 14) which are distanced to one another along the longitudinal axis (18) of the rotor shaft (11) and which project away from the shaft in the expanded condition of the rotor, as well as at least two limp rib elements (25, 26, 27, 28, 29, 30) which run at a distance to one another from one erection element (12, 13, 14) at least up to a further erection element, wherein a limp membrane (10) is held between the rib elements, which is tautened in the expanded condition of the rotor. A good compressibility of the rotor with low counter-forces, as well as a simple setting-up of the rotor may be achieved by the membrane-like design of the rotor blades. The membrane may for example be manufactured with the immersion method.

17 Claims, 10 Drawing Sheets

Figure 1:
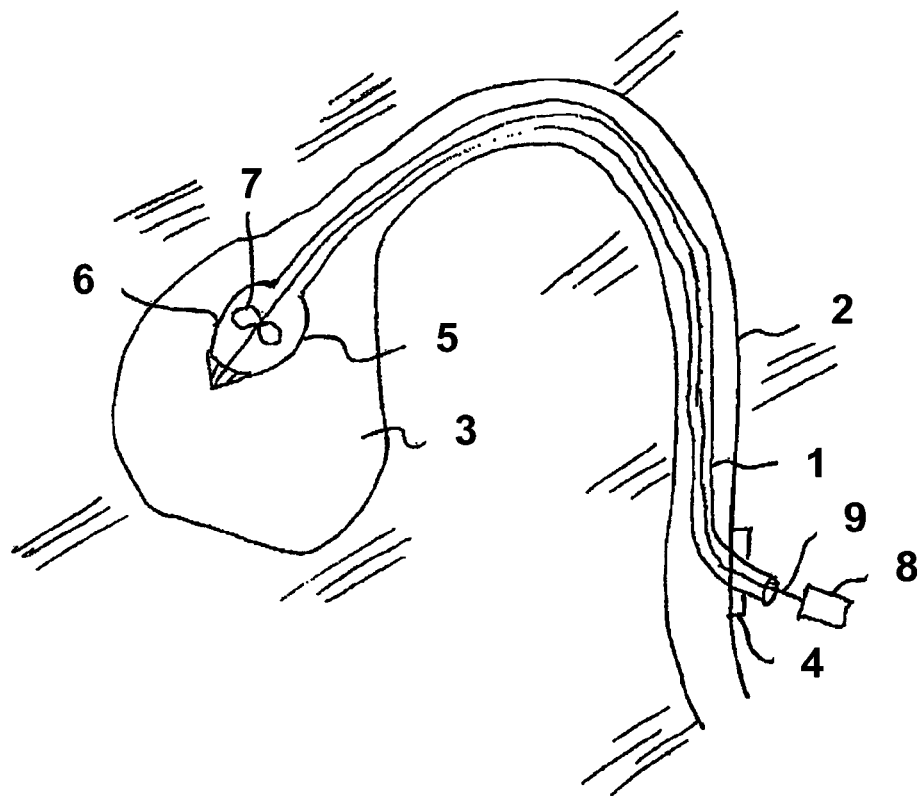

(51) Int. Cl.
  *A61M 1/10* (2006.01)
  *F04D 29/18* (2006.01)
  *F04D 29/24* (2006.01)

(56) References Cited

U.S. PATENT DOCUMENTS

| | | |
|---|---|---|
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Scmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 * | 11/2003 | Evans et al. ............ 606/159 |
| 6,719,791 B1 | 4/2004 | Nusser |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,927,068 B2 | 4/2011 | McBride et al. |
| 7,934,909 B2 | 5/2011 | Neusser et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0132747 A1 * | 6/2008 | Shifflette ............ 600/16 |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 69407869 T2 | 4/1998 |
| DE | 29804046 U1 | 6/1998 |
| DE | 69017784 T3 | 4/2000 |
| DE | 69427390 T2 | 9/2001 |
| DE | 100 59 714 | 5/2002 |
| DE | 10059714 C1 | 5/2002 |
| DE | 10108810 A1 | 8/2002 |
| DE | 10155011 A1 | 5/2003 |

(56) References Cited

FOREIGN PATENT DOCUMENTS

| | | |
|---|---|---|
| DE | 69431204 T2 | 8/2003 |
| DE | 10336902 B3 | 8/2004 |
| DE | 102010011998 A1 | 9/2010 |
| EP | 04801102 A1 | 4/1992 |
| EP | 0560000 A2 | 9/1993 |
| EP | 0768900 | 4/1997 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2047872 | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 | 10/2000 |
| WO | 0107760 A1 | 2/2001 |
| WO | 0107787 A1 | 2/2001 |
| WO | 0183016 A2 | 11/2001 |
| WO | 03057013 A2 | 7/2003 |
| WO | 03103745 A2 | 12/2003 |
| WO | WO 03/103745 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A2 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

OTHER PUBLICATIONS

International Preliminary Report on Patentability mailed Sep. 29, 2011 for Application No. PCT/EP2010/001889.

* cited by examiner

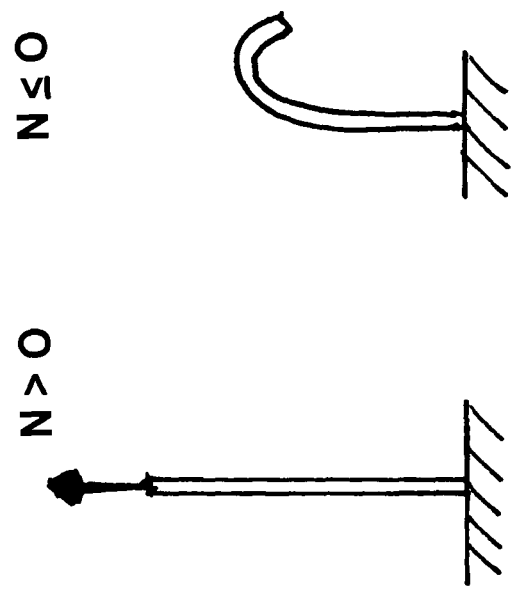

FLUID PUMP

The invention lies in the field of medical technology, and in particular of precision engineering, where the precise shaping and manufacture of technical components of a small construction size is at the forefront.

This problem plays an important role for example with the construction of micro-pumps, which on the one hand need to be of a high-performance and reliable, but on the other hand are to combine a minimal construction size with an acceptable delivery performance, and this with as low as possible costs.

Moreover, with many medical applications as well as with other special applications, there exists the requirement for such a pump to be temporarily reduced in size for introduction into a difficultly accessible space, in order to be able to accordingly increase its size again after the introduction into the application space. Added to this is the demand in the medical field for the pump, after the application for example in a space within a human body, to also be reduced in size again, in order to be able to remove it from the body without major operations.

In medical technology, this object occurs for example with the provision of catheter pumps which may be introduced into the bloodstream, and may deliver blood, e.g. in a heart chamber.

Such fluid pumps which may be changed in particular with regard to their diameter, are for example known in designs which use so-called shape-memory materials, wherein the design at a first temperature obtains a certain shape and automatically changes this on transition to another temperature.

With the use of such materials, apart from the high costs of the starting materials however, one must consider a series of additional mechanical problems, which specifically relate to the memory characteristics and may be functionally disadvantageous.

Expandable and compressible fluid pumps are already known from the state of the art. The patent document DE 100 59 714 C1 for example shows a pump which together with the pump drive may be pushed through a blood vessel. The blood flows there through a cannula whose diameter may be expanded or compressed for changing the flow conditions.

A further design of a blood pump is to be deduced from WO 03/103745 A2, whose rotor may be radially compressed and expanded. According to the publication document, different designs are suggested for achieving the expansion ability. For example, by way of different parts of the catheter which may be displaced to one another, one may achieve a compression of the pump housing and a radial expansion which this entails, after the introduction into the body of a patient. Moreover, disclosed is also the possibility of producing a helix structure of a wire by way of rotating a drive shaft with respect to a wire located in the catheter, said wire forming the outer radial delimitation of a rotor blade.

WO 03/103745 A2 furthermore discloses a rotor structure with a plurality of blades which are stiff per se and are pivotably articulated on a central part and which assemble themselves on operation of the pump and thus produce a fluid pressure.

A pump is known for EP 0 768 900 B1, with which rotor blades are articulated onto a shaft within a pump housing, in a manner such that in the idle condition they are folded onto the shaft, and on operation may be erected perpendicularly to the shaft, in order to deliver the fluid.

According to the known state of the art, thus a series of mechanisms is known, which permit an active assembly of a delivery blade/rotor blade, by way of actuation elements, wherein the surface of the rotor blade in each case is deformed and/or unfolded.

It is the object of the present invention to provide a fluid pump whose rotor is constructed in an as simple as possible manner, in order to permit a secure functioning during operation as well as a simple and reliable expansion as well as compression, with as little as possible counter-force.

According to the invention, this object is achieved by the features of patent claim 1.

Thereby, the invention is based on the concept of a rotor blade of the pump comprising at least two erection elements, which are fastened distanced to one another in the longitudinal direction of the rotor shaft, in a movable manner on this and which carry limp rib elements for example rib wires or rib strips, which run at a distance to one another between at least two erection elements, wherein a limp membrane is held between the rib elements.

"Limp" denotes "rope-like" mechanical properties. If tension (=pulling force) is applied, the ribs are very stiff in terms of elongation (see FIG. 14a). However, if no tension (=pulling force) is applied, the rib elements are very flexible (i.e. have a high flexural elasticity; i.e. bending is very easy). If such a limp rib element is erected (as shown in FIG. 14b) and no pulling force is applied, it bends (only due to its own weight) as it is unstable and has a low flexural modulus. Thus, as shown in FIG. 14b, if a pulling force equal to or less than 0 N is applied, the rib element bends (except for the case that the rib element is hanging or lying on a plain surface).

These limp rib elements are different to rib elements as they may be known in the prior art. It is important for the invention that the at least two erection elements which are fastened to one another in the longitudinal direction of the rotor shaft are relatively stiff compared to the limp rib elements. Thus, the instant construction does not show a (homogeneous) frame structure in which the rib elements and the erection elements have similar mechanical properties. On the contrary, the limp rib elements should have a low flexural modulus in order to comply with the membrane, whereas the erection elements provide stability. In a preferred embodiment, the geometry and/or material of the erection elements is different from the material of the limp rib elements. Whereas the erection elements have to be rather stiff in terms of flexural elasticity, the rib elements have to be rather flexible (like a flexible wire/rope/ribbon). The characteristics of these limp elements hereby lead to a significantly more compliant behavior of the rotor as a reaction to the flow pressure. By way of this, the rotor with regard to its shape adapts to the local flow pressure in a manner such that pressure peaks are avoided and a more uniform pressure distribution sets in. As a result, the forces acting on the fluid are smaller, which particularly with the application in blood pumps leads to a reduced damage of the blood. With a suitable design, the parts of the rotor blade may also flutter, which effects additional eddies, which in contact with body fluids such as blood minimizes the problem of formation of clotting.

In the compressed condition of the rotor, the erection elements are applied as far as possible onto the rotor shaft, so that the pump delivers almost no fluid, even with a rotation of the rotor. When the erection elements are erected, i.e. at least partly moved away from the rotor shaft, then the rib elements running between these tension (tauten) a membrane, which forms the essential surface of the rotor blade/impeller of the pump.

It is due to the design according to the invention that the rotor blade on the one hand becomes particularly small in the compressed condition, so that it may be accommodated in a space-saving manner, and on the other hand, in the set-up condition, it provides an adequately large and adequately stabilized surface, by way of which the fluid may be delivered on operation of the rotor. The rib elements stabilize the membrane in a manner such that a tearing is prevented despite the very thin design of the membrane. The rib elements may form the outer delimitation of the membrane and thus also prevent a tearing of the membrane from the outer side, for example due to overload or mechanical injuries.

The rib elements for their part are held between the erection elements, which due to their movement ability permit the folding out of the rotor blade.

The erection elements for example are connected in each case with a first of their ends to the rotor shaft in a pivotable manner. Thereby, each erection element may be stiff per se and be connected to the rotor shaft or to a hub, either by way of a bearing or a film joint.

Simultaneously, the pivoting movement of the erection elements may be limited by way of a suitable design of the joint or film joint or of the bearing, in a manner such that these erection elements on operation, on the one hand are set up (erected) by way of the fluid counter-pressure of the fluid to be delivered, but on the other hand such that their set-up movement is limited in the condition of the largest expansion of the rotor blade, so that the rotor blade is stabilized on operation.

The erection elements may be stiff per se or may also be bendable up to a certain shape limit.

The erection elements may be pivotable in the peripheral direction with respect to the rotor shaft, or also in a plane which contains the longitudinal axis of the rotor shaft.

In any case, the articulation of the erection elements may be designed in a manner such that these in the idle condition bear on the rotor shaft approximately parallel to this, and are at least partly radially spread away from this in the operating condition.

Advantageously, the erection elements may have a shape which in the compressed condition produces a force which, given a rotation of the rotor in the operational direction, acts on these erection elements and effects an assembly of these erection elements, due to the counter pressure of the fluid.

This shape may for example be achieved by way of beveling or a blade shape or propeller shape of the erection elements.

The erection elements may advantageously be offset to one another in the peripheral direction along the longitudinal axis of the rotor shaft. By way of this, with two or more erection elements belonging to a single rotor blade or a single impeller, a helix-like shape is made possible with respect to the membrane held between them.

The membrane may be connected to at least two rib elements advantageously in a fixed manner, and these rib elements may for example be designed as wires.

Thereby, the rib elements may advantageously be connected to at least two erection elements in a tension-proof manner, for example to the erection elements which are outermost seen in the longitudinal direction of the rotor shaft The rib elements may also be connected in a tension-proof manner to the erection elements lying therebetween, in as much as such exist, but it is also conceivable for the rib elements to only be guided in these and to be able to move a little with respect to these middle erection elements.

Thus, by way of the length of the rib elements one may also define how far the individual erection elements may be deflected on operation of the motor, for shaping an erected membrane. The limitation of the movement of the erection elements may thus be ensured by way of a suitable choice of rib elements, in particular their length.

The rib elements may thereby advantageously run parallel to one another, in particular in a spiral manner around the rotor shaft. One may also envisage the rib elements being concentrated in the region of particularly high loading of the membrane on operation.

The rib elements may be manufactured from the same material as the membrane, for example a plastic, and be designed in a strand-like manner. They may however also consist of a firmer, less stretchable material than the membrane, for example another plastic or of a metal. The membrane is advantageously designed in a more elastically and easily deformable manner than the rib elements.

For producing an as large as possible pump pressure, one advantageously envisages the membrane sealingly terminating on the rotor shaft. By way of this, the flow of fluid past the membrane in the region of the rotor shaft is prevented, which would lead to pressure loss and a performance loss of the pump.

Apart from a fluid pump of the type mentioned above with a suitable design of the rotor, the invention also relates to a method for manufacturing a rotor for such a pump, with which by way of immersion of the rib elements into a fluid, a fluid membrane is formed between these, which solidifies after removal from the fluid. This is a method for manufacturing a rotor for a fluid pump in particular liquid pump, with a rotor, with a rotor shaft and with at least one rotor blade for delivering fluid, wherein the rotor with regard to its diameter may be changed between a first, compressed condition, and a second expanded condition, wherein the at least one rotor blade comprises at least two erection elements which are distanced to one another along the longitudinal axis of the rotor shaft and which project away from the shaft in the expanded condition of the rotor, as well as (preferably, but not necessarily, at least two, preferably limp) rib elements which run at a distance to one another from one erection element at least up to a further erection element, wherein a limp membrane is held between the rib elements, which is tautened in the expanded condition of the rotor, characterized in that a membrane is formed by the immersion of the rib elements into a fluid, between these, said membrane solidifying after removal from the fluid.

The membrane may be manufactured in a simple manner by way of this manufacturing process and may also be connected to the rib elements in a firm manner in the same working procedure. The desired distribution of the rib elements on the membrane surface may be fixed in at least in two dimensions in the same run.

Of course, the membrane may also be manufactured by way of bonding a premanufactured film onto the rib elements or by way of a similar joining technique.

Figure 2:
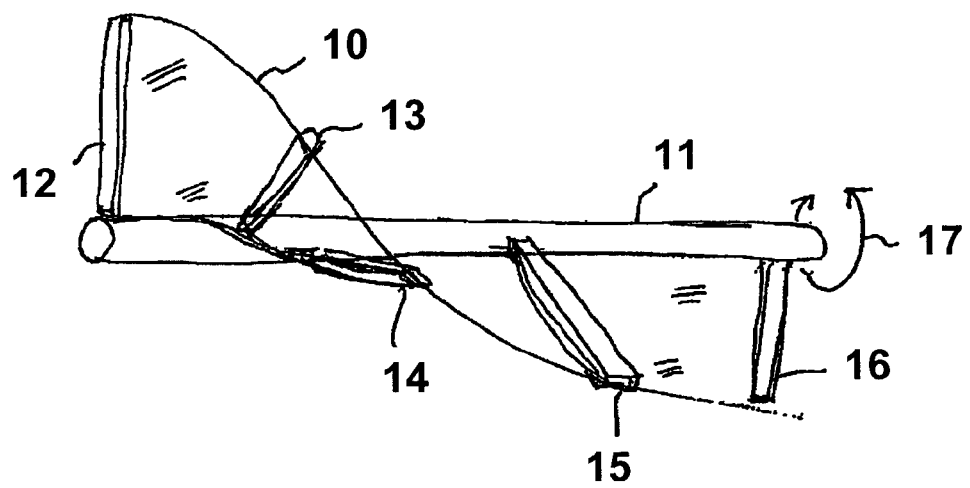
Figure 3:
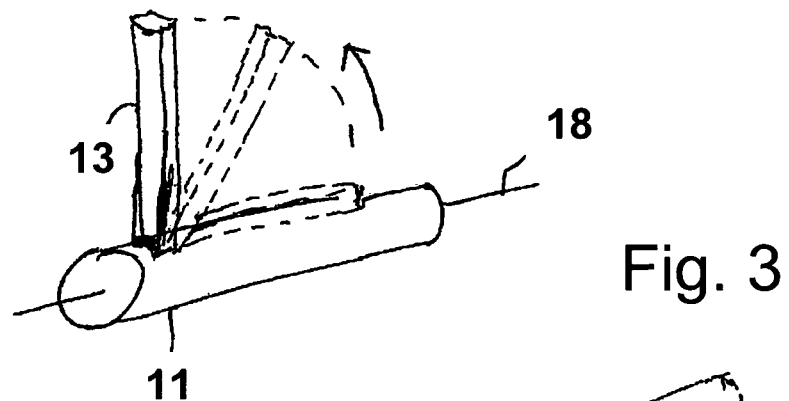
Figure 4:
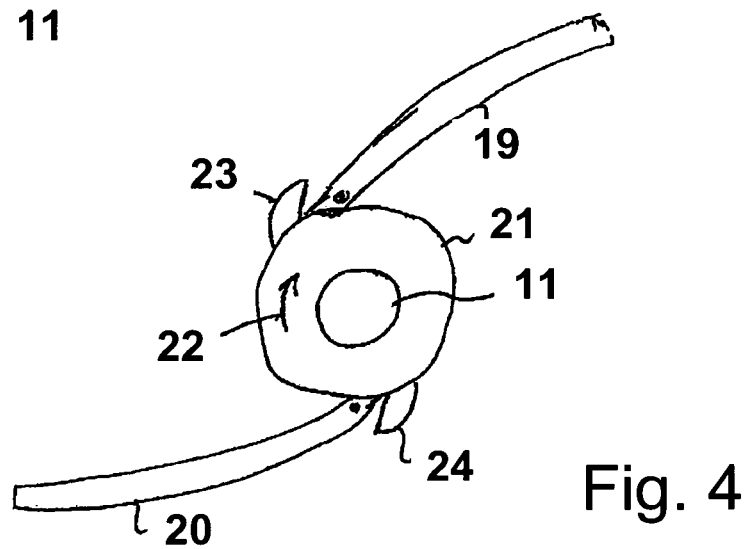
Figure 5:
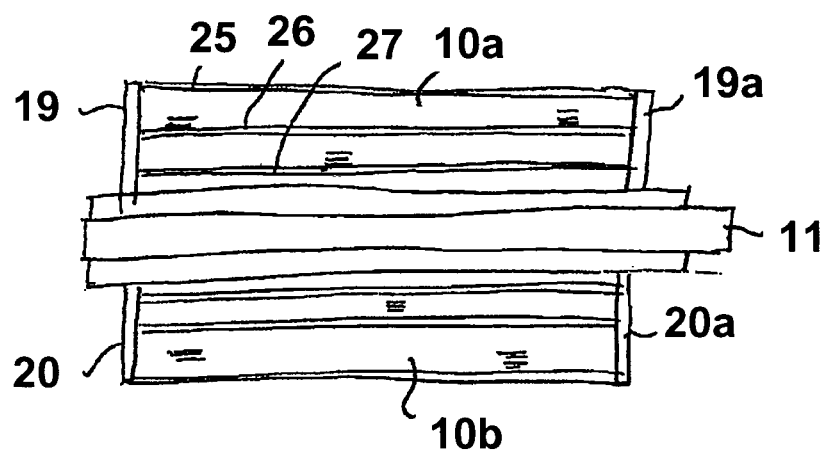
Figure 6:
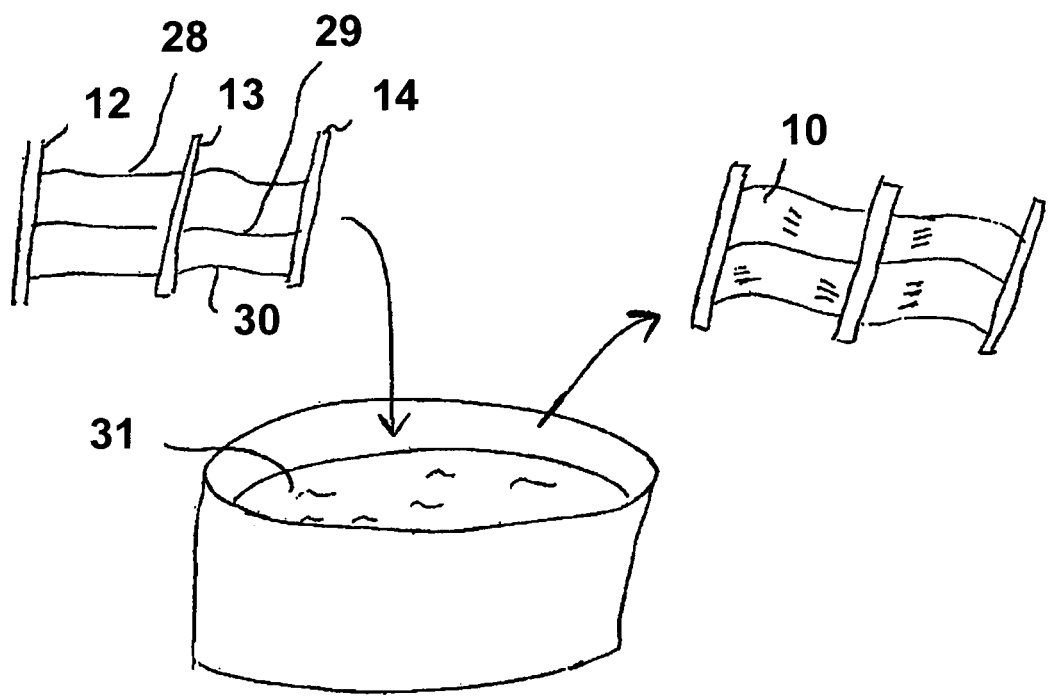
Figure 12:
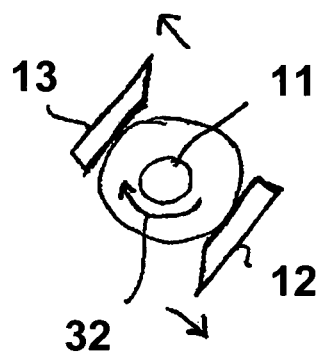
Figure 7:
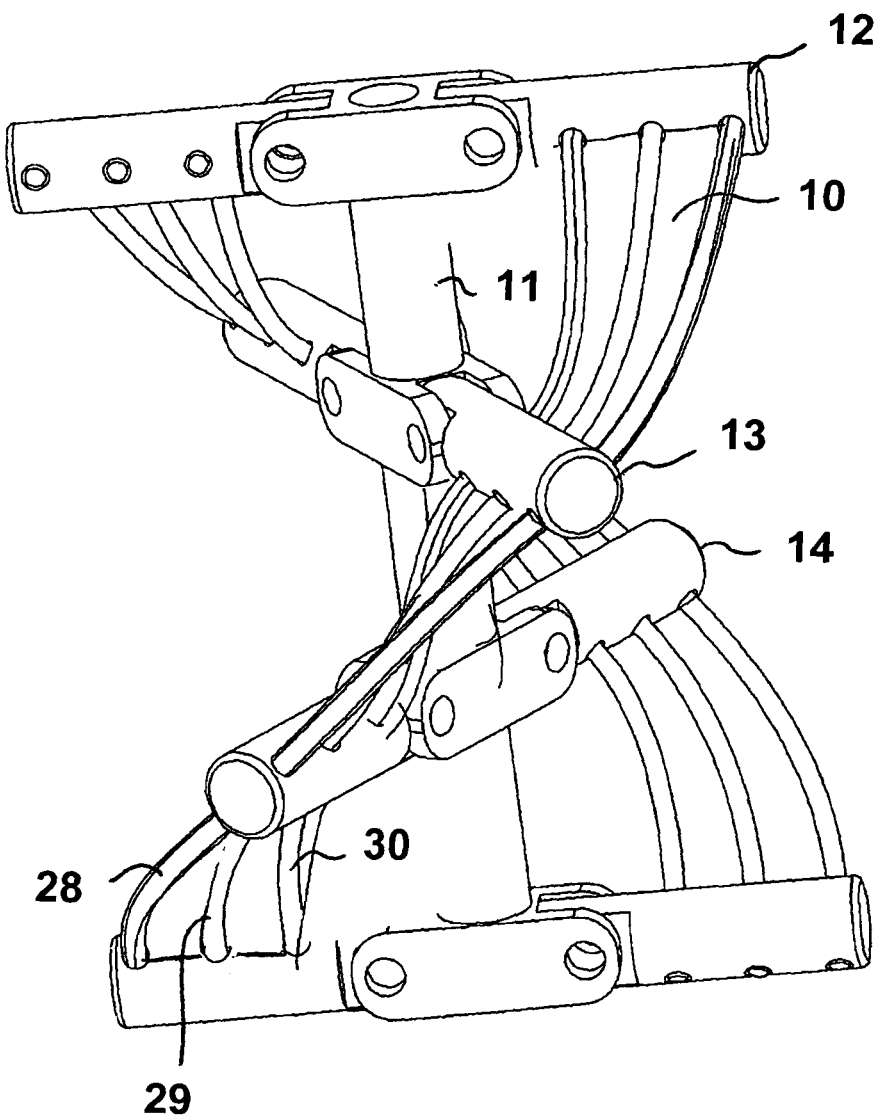
Figure 8:
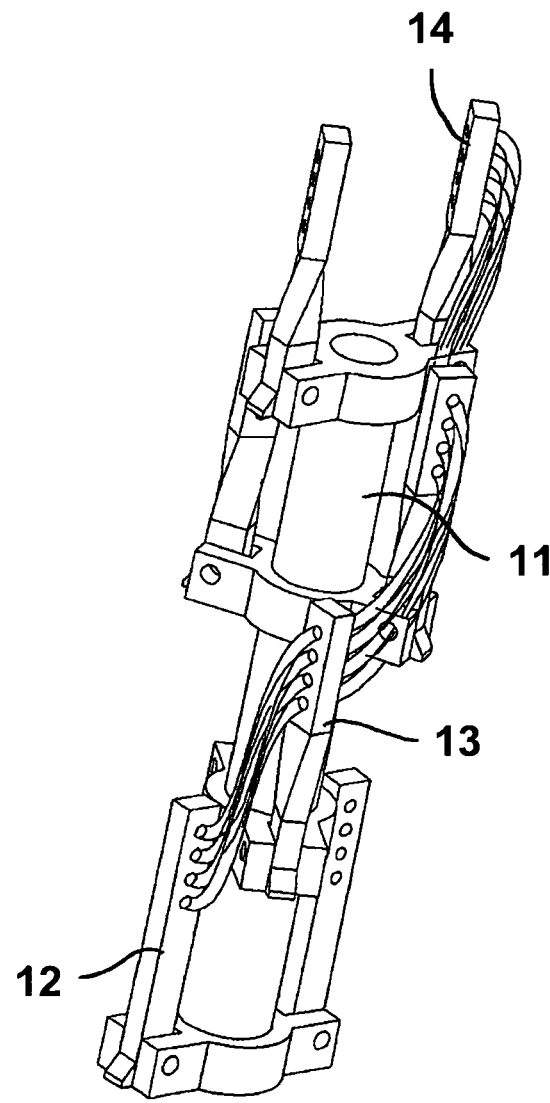
Figure 9:
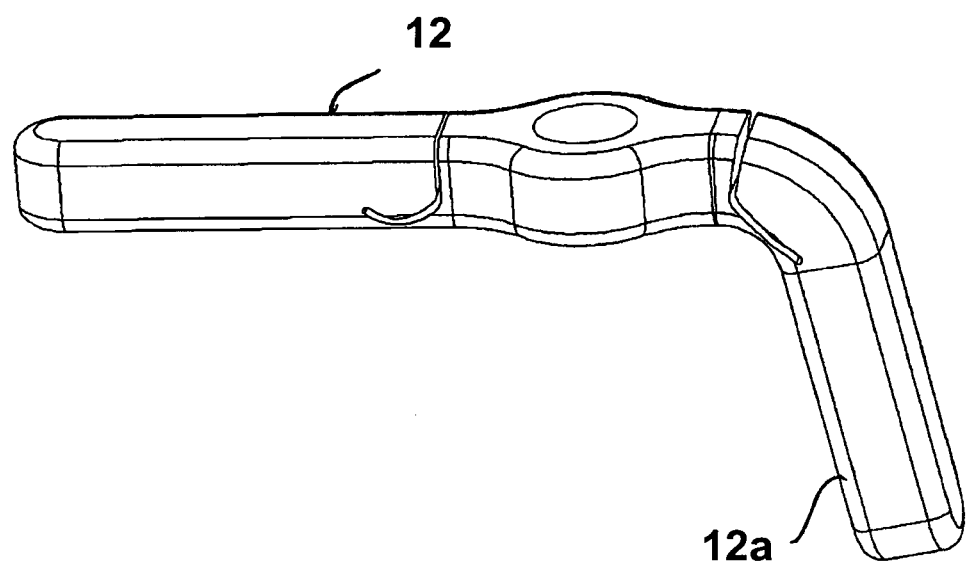
Figure 10:
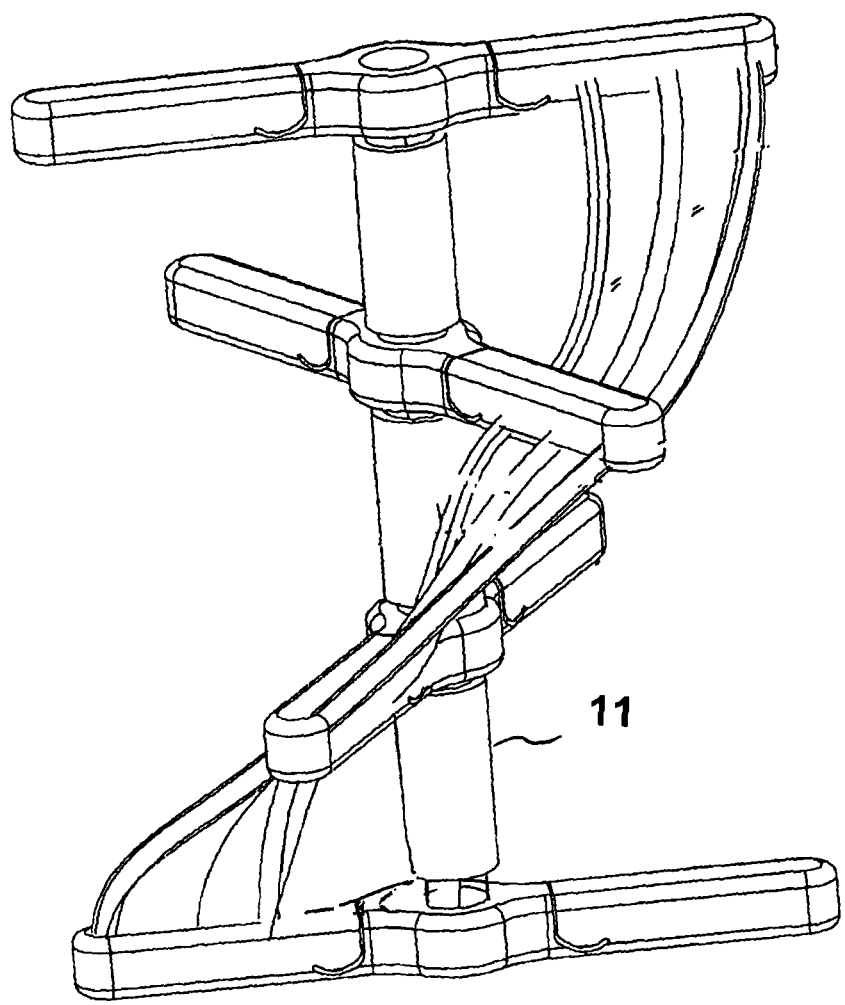
Figure 11:
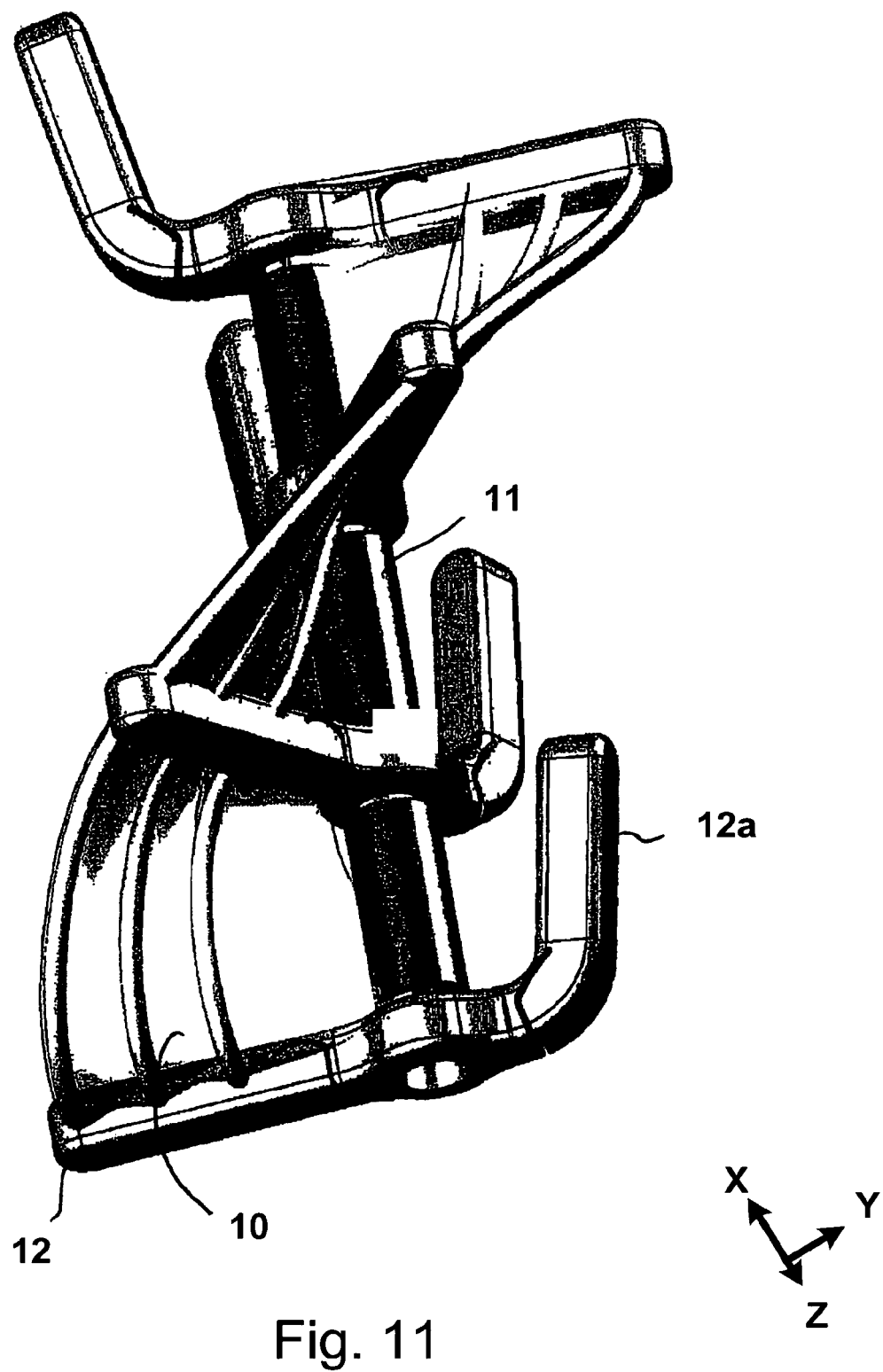
Figure 13:
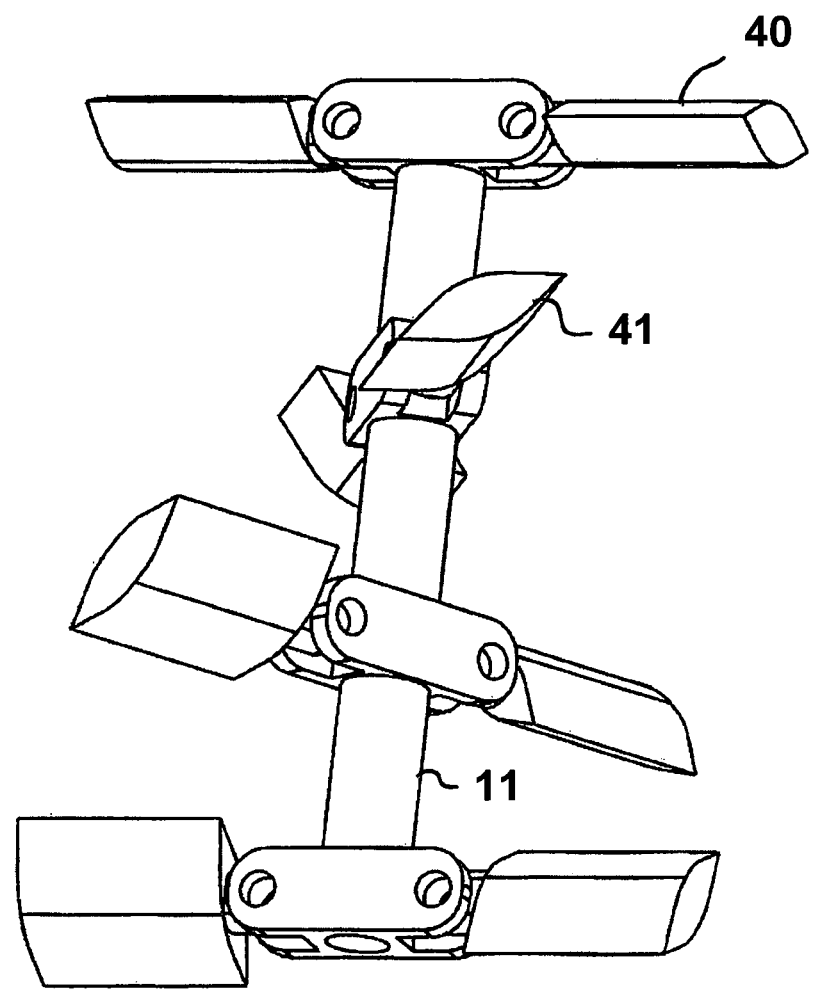

The invention is hereinafter shown and subsequently described by way of one embodiment example and by way of several drawings. Thereby there are shown in:

FIG. 1 in a section, one application of a catheter provided with a pump,

FIG. 2 by way of example, a pump rotor with a rotor blade,

FIG. 3 a rotor blade as well as an erection element,

FIG. 4 a plan view of a rotor shaft with a hub and two rotor blades,

FIG. 5 a transverse view of the rotor of FIG. 4,

FIG. 6 schematically, the manufacturing procedure for a rotor blade with an immersion method for manufacturing a membrane, FIG. 7 a three-dimensional view of a pump rotor in an expanded form, FIG. 8 a three-dimensional view of a pump rotor in a compressed form with folded-on erection elements, FIG. 9 an individual erection element, FIG. 10 a further example of a pump rotor in the expanded shape, FIG. 11 a pump rotor in an expanded form, wherein only half of the erection elements is set up, FIG. 12 in a plan view, a rotor with two profiled erection elements, as well as FIG. 13 a rotor with set-up, propeller-like erection elements, but without a membrane, in a perspective view.

FIGS. 14a, b schematic drawings for showing mechanical properties of the limp rib elements.

FIG. 1 shows a catheter 1 which is introduced into a human blood vessel 2 up to a heart chamber 3 and projects through a lock 4 out of the vessel 4. The catheter together with the micro-pump 5 is led through this lock into the heart chamber 3. For this purpose, on insertion, the pump is set into a compressed condition in which the pump housing 6 as well as the rotor 7 is reduced in size with respect to its diameter. The design of the rotor and of the pump housing envisages no large restoring forces arising, which have the tendency to expand the pump against the force of the vessel walls.

As soon as the pump 5 is introduced into the heart chamber 3, the rotor 7 may be set into rotation by way of the shaft 9 led through the catheter 1, in order to deliver fluid. Simultaneously, at least one rotor blade 10 is set up as shown in FIG. 2, either by way of mechanical actuation or by way of its own rotation, and the effect of the fluid counter-pressure on starting operation of the pump. The shaping and the mechanisms will be dealt with on more detail further below.

FIG. 2, in a three-dimensional representation, shows a rotor shaft 11 with erection elements 12, 13, 14, 15, 16 as well as a membrane 10 stretched out between the erection elements 12 to 16, which forms the rotor blade or the impeller. The membrane 10 in the completely set-up or erected condition forms a helix-like structure, so that the pump rotor delivers fluid on rotation in the axial direction. The rotation direction of the shaft is indicated by the arrow 17.

The erection elements 12 to 16 according to the invention are moveably connected to the rotor shaft 11, and in the idle condition, i.e. in the compressed condition, are folded onto this.

For this, FIG. 3 shows the case in which the erection element 13 may be folded within a plane which contains the longitudinal axis 18 of the rotor shaft 11. Various possible positions of the erection element 13 are represented in a dashed manner. The erection element 12 may be fastened on the shaft 11 in a pivotable manner by way of a film joint or by way of a bearing.

FIG. 4 shows a different type of design of the erection elements 19, 20 in a plan view of the shaft 11, which carries a hub 21.

If the rotor is rotated in the direction of the arrow 22, then the erection elements 19, 20 are set up further by way of the fluid counter-pressure, until they abut the abutments 23, 24. In this position, the fluid opposes the rotor with the greatest resistance.

In each case, at least one further erection element 19a, 20a is provided with the erection elements 19, 20, and rib elements 25, 26, 27 are fastened between these further erection elements. A membrane 10a, 10b is fastened between the rib elements 25, 26, 27 (FIG. 5).

The represented rotor may then be used for a radial pump if the erection elements 19, 19a and 20, 20a are not offset to one another in the peripheral direction of the shaft 11.

If the erection elements 19, 19a are offset to one another in the peripheral direction of the shaft 11, then the respective membrane 10a, 10b assumes a helix-like shape and the pump rotor also be used for the at least partial axial delivery of a fluid.

The possible manufacture of a rotor blade is represented by way of FIG. 6, wherein one assumes three erection elements 12, 13, 14, between which rib elements 28, 29, 30 in the form of wires or plastic strands are fastened. This premanufactured part is immersed into a fluid 31, which for example may consist of a resin or contain a resin.

The viscosity of the fluid 31 and the distances between the rib elements 28, 29, 30 are set in a manner such that a fluid film forms between the rib elements due to surface tension, which is stable for a while, until the fluid hardens and solidifies by way of curing or cooling.

The number of the rib elements when required may also be two or more than three, instead of the three.

FIG. 7 shows a three-dimensional view of a pump rotor with a shaft 11, from which three erection elements 12, 13, 14 project at a maximal right angle.

Rib elements 28, 29, 30 are fastened between the erection elements 12, 13, 14, between which rib elements a membrane is formed. By way of the rotation of the erection elements 12, 13, 14 this membrane similarly to the rib elements, assumes a helix-like structure, which on rotation of the pump rotor leads to an axial delivery of the fluid.

The rotor of FIG. 7 is shown in the compressed form in FIG. 8, wherein the erection elements 1, 13, 14 as well as the respective erection elements which lie opposite these and are not shown in more detail in FIG. 7, are folded in each case parallel to the shaft 11. The rib elements in this condition likewise run parallel to the rotor shaft 11, and the membrane hardly offers any resistance to a rotation in this condition.

FIG. 9 in detail shows two erection elements 12, 12a which in the installed condition lie diametrally opposite one another on a shaft 11 and may be folded away by 90°.

FIG. 10 shows eight such erection elements, of which in each case two lie diametrally opposite one another on the shaft 11 and wherein corresponding rib elements are fastened to a membrane only between fours of the erection elements. The membrane runs in a helix-like manner and bears on the shaft in the region of this. The remaining erection elements are advantageously yet provided with a membrane which likewise has a helix-like shape, for increasing the efficiency of the pump.

Here, the representation of further erection elements, rib elements and coatings of a further rotor blade which is offset with respect to the first one have been omitted in the representation, for the purpose of a better overview.

FIG. 11 shows a rotor with a single rotor blade 10, which is fastened on four erection elements 12. The erection elements 12a, which in each case lie diametrally opposite the individual erection elements 12 with respect to the shaft 11, carry no membrane and in operation also remain folded onto the shaft, in order to keep the eddy loss in the fluid as small as possible.

Here too, the rib elements and coatings have only been shown on one side for the purposes of a better overview.

The folded rib elements by way of representation are to illustrate how the complete rotor looks with folded elements.

FIG. 12 in a plan view shows a rotor shaft 11 which on operation rotates in the direction represented by the arrow 32, wherein the erection elements 12, 13 are profiled in a manner such that at the beginning, on starting operation of the pump, a radial outwardly directed force is exerted on the erection elements, already due to the fluid counter-pressure, said force effecting a spreading of the erection elements 13, 14 away from the shaft.

If the erection elements 12, 13 are spread out to a small extent, then the membrane between them also begins to set itself up and produce a fluid counter-pressure, which rapidly effects a further set-up of the rotor blade until the setting-up movement reaches its limits due to a mechanical abutment or the limited deformability of the erection elements.

FIG. 13 finally shows a rotor with erected, propeller-like erection elements 40, 41 but without membrane, in the perspective view.

The design according to the invention and the manufacturing concept of the represented rotor blades, with a low effort, permits the manufacture of efficiently applicable rotor blades with rib elements and membranes, which may be applied in a reliable manner. A high compressibility of the rotor with a low counter-force may be achieved, since the rotor blades with the exception of the erection elements consist of limp materials. The flow effects on starting operation of the pump are utilized. If the rotor is to be compressed again, then a rotation opposite to the operating direction is useful in order to fold the erection elements onto the rotor shaft 11 again.

(Description of FIGS. 14a, 14b: see above.)

The invention claimed is:

1. A fluid pump, comprising:
   a rotor,
   a rotor shaft and
   at least one rotor blade for delivering fluid,
   wherein the rotor with regard to its diameter is changed between a first, compressed condition, and a second expanded condition,
   wherein the at least one rotor blade comprises at least two erection elements which are distanced to one another along the longitudinal axis of the rotor shaft and which project away from the shaft in the expanded condition of the rotor, as well as at least two limp rib elements which run at a distance to one another from one erection element at least up to a further erection element, wherein a limp membrane is held between the rib elements, which is tautened in the expanded condition of the rotor.

2. A fluid pump according to claim 1, characterized in that the erection elements in each case with a first of their ends are fastened on the rotor shaft, wherein the respective other end is movable with respect to the rotor shaft.

3. A fluid pump according to claim 2, characterized in that the erection elements in each case with their first end are pivotably connected to the rotor shaft.

4. A fluid pump according to claim 3, characterized in that the erection elements are connected to the rotor shaft in each case by way of a bearing or a film joint.

5. A fluid pump according to claim 2, characterized in that the erection elements are pivotable with respect to the rotor shaft in its peripheral direction.

6. A fluid pump according to claim 2, characterized in that the erection elements are pivotable with respect to the rotor shaft in a plane, which contains the longitudinal axis of the rotor shaft.

7. A fluid pump according to claim 1, characterized in that the erection elements have a shape, which with a rotation of the rotor in the operating direction produces a force acting on the erection elements and effecting the erection of the erection elements, due to the fluid counter-pressure.

8. A fluid pump according to claim 1, characterized in that the erection elements are offset to one another in the peripheral direction along the longitudinal axis of the rotor shaft.

9. A fluid pump according to claim 1, characterized in that the membrane is firmly connected to at least two rib elements.

10. A fluid pump according to claim 9, characterized in that the rib elements are connected in a tension-proof manner to at least two erection elements.

11. A fluid pump according to claim 1, characterized in that the erection elements are pivotable in a limited manner up to a mechanical abutment.

12. A fluid pump according to claim 1, characterized in that the rib elements run essentially parallel to one another.

13. A fluid pump according to claim 12, characterized in that the rib elements run around the rotor shaft in an essentially spiral manner.

14. A fluid pump according to claim 1, characterized in that the membrane sealingly terminates on the rotor shaft.

15. A method for manufacturing a rotor for a fluid pump, comprising:
   a rotor
   a rotor shaft and
   at least one rotor blade for delivering fluid,
   wherein the rotor with regard to its diameter is changed between a first, compressed condition, and a second expanded condition,
   wherein the at least one rotor blade comprises at least two erection elements which are distanced to one another along the longitudinal axis of the rotor shaft and which project away from the shaft in the expanded condition of the rotor, wherein at least two limp rib elements run at a parallel distance to one another from one erection element to the next erection element,
   wherein a limp membrane is held between the rib elements, which is tautened in the expanded condition of the rotor, characterized in that the limp membrane is formed by the immersion of the rib elements into a fluid, between these, said membrane solidifying after removal from the fluid.

16. A method for manufacturing a rotor for a fluid pump according to claim 1, characterized in that firstly the rib elements are aligned and that a membrane is thereafter fastened to the rib elements.

17. A fluid pump according to claim 1, characterized in that the membrane is firmly connected to at least two rib wires.

* * * * *